United States Patent
Nishide

(10) Patent No.: US 11,842,815 B2
(45) Date of Patent: Dec. 12, 2023

(54) ENDOSCOPE SYSTEM, PROCESSOR, DIAGNOSTIC SUPPORT METHOD, AND COMPUTER PROGRAM

(71) Applicant: HOYA CORPORATION, Tokyo (JP)

(72) Inventor: Akihiko Nishide, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 166 days.

(21) Appl. No.: 17/632,443

(22) PCT Filed: Jan. 6, 2021

(86) PCT No.: PCT/JP2021/000217
§ 371 (c)(1),
(2) Date: Feb. 2, 2022

(87) PCT Pub. No.: WO2021/141048
PCT Pub. Date: Jul. 15, 2021

(65) Prior Publication Data
US 2022/0293268 A1    Sep. 15, 2022

(30) Foreign Application Priority Data

Jan. 7, 2020 (JP) .................................. 2020-000868

(51) Int. Cl.
A61B 1/06 (2006.01)
A61B 1/00 (2006.01)
(Continued)

(52) U.S. Cl.
CPC ....... *G16H 50/20* (2018.01); *A61B 1/000094* (2022.02); *A61B 1/000095* (2022.02);
(Continued)

(58) Field of Classification Search
CPC ........ A61B 1/000094; A61B 1/000095; A61B 1/000096; A61B 1/0655; G06T 7/0012;
(Continued)

(56) References Cited

U.S. PATENT DOCUMENTS

2012/0033105 A1    2/2012 Yoshino
2012/0105612 A1    5/2012 Yoshino
(Continued)

FOREIGN PATENT DOCUMENTS

JP    08-110563    4/1996
JP    10-9819    1/1998
(Continued)

OTHER PUBLICATIONS

Feb. 21, 2023 Japanese Office Action in Japanese patent application No. 2021-570068 and English translation thereof.
(Continued)

*Primary Examiner* — Sherrie Hsia
(74) *Attorney, Agent, or Firm* — GREENBLUM & BERNSTEIN, P.L.C.

(57) ABSTRACT

Provided are an endoscope system, a processor, a diagnostic support method, and a computer program. A plurality of images are captured at different focal positions on an object, an evaluation value indicating a degree of focus is calculated for each of corresponding sub-regions among the plurality of captured images, a captured image including a sub-region having the highest degree of focus is determined among the plurality of captured images based on the calculated evaluation value, a distance to a region on the object corresponding to the sub-region is calculated, distance information is generated by calculating a distance to a plurality of regions on the object corresponding to the sub-region, a feature region is extracted from the captured image, diagnostic support information for the object is generated based on the distance information and a feature parameter associated with the feature region, and the generated diagnostic support information is output.

11 Claims, 11 Drawing Sheets

(51) Int. Cl.
  *G06T 7/00* (2017.01)
  *G16H 50/20* (2018.01)
  *G16H 30/40* (2018.01)
(52) U.S. Cl.
  CPC ...... *A61B 1/000096* (2022.02); *A61B 1/0655* (2022.02); *G06T 7/0012* (2013.01); *G16H 30/40* (2018.01); *G06T 2207/10068* (2013.01); *G06T 2207/20081* (2013.01)
(58) Field of Classification Search
  CPC . G06T 2207/10068; G06T 2207/10148; G06T 2207/20081; G16H 50/20; G16H 30/40
  USPC .............................................. 348/68, 65, 69
  See application file for complete search history.

(56) References Cited

U.S. PATENT DOCUMENTS

| | | | |
|---|---|---|---|
| 2015/0139534 | A1 | 5/2015 | Komatsu |
| 2017/0265725 | A1 | 9/2017 | Ichikawa et al. |
| 2018/0296064 | A1 | 10/2018 | Kanda et al. |
| 2019/0216308 | A1 | 7/2019 | Senaras et al. |
| 2022/0400938 | A1* | 12/2022 | Arai ................. A61B 1/000095 |

FOREIGN PATENT DOCUMENTS

| | | |
|---|---|---|
| JP | 11-337845 | 12/1999 |
| JP | 2002-065581 | 3/2002 |
| JP | 2002-238887 | 8/2002 |
| JP | 2012-039255 | 2/2012 |
| JP | 2012-095828 | 5/2012 |
| JP | 2014-161355 | 9/2014 |
| JP | 2015-096812 | 5/2015 |
| JP | 6125740 | 5/2017 |
| JP | 2019-534726 | 12/2019 |
| WO | 2016/088186 | 6/2016 |
| WO | 2017/090166 | 6/2017 |

OTHER PUBLICATIONS

International Search Report issued in International Bureau of WIPO Patent Application No. PCT/JP2021/000217, dated Mar. 16, 2021, along with an English translation thereof.

Jul. 18, 2023 Japanese Office Action in Japanese Application No. 2021-570068 and translation thereof.

* cited by examiner

FIG. 12
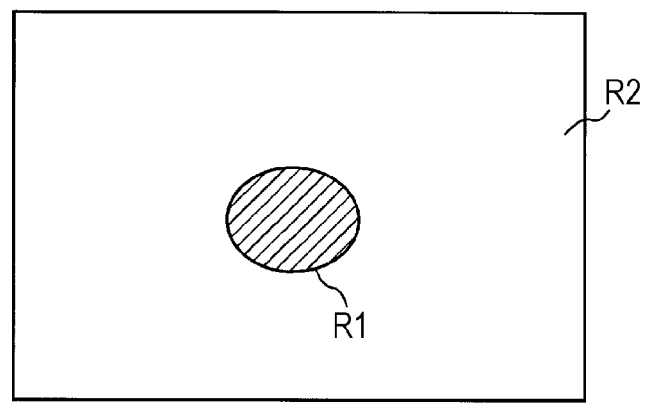
DISPLAY IN THREE DIMENSIONS
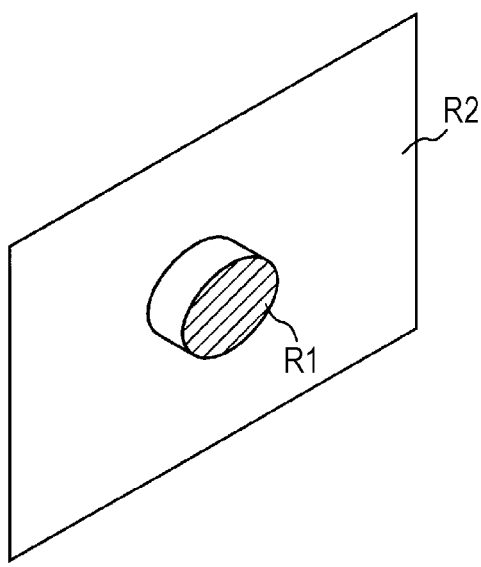

ENDOSCOPE SYSTEM, PROCESSOR, DIAGNOSTIC SUPPORT METHOD, AND COMPUTER PROGRAM

TECHNICAL FIELD

The present invention relates to an endoscope system, a processor, a diagnostic support method, and a computer program.

BACKGROUND ART

Known endoscope systems are used for examining the inside of lumens such as esophagi and intestines of humans. Such a type of endoscope system includes an endoscope processor that processes an image of an object captured by an electronic scope. The endoscope processor performs color conversion, noise reduction, and other image processing on pixel signals and causes a monitor to display an operator-friendly (or doctor-friendly) examination image (see, for example, Patent Literature 1).

CITATION LIST

Patent Literature

Patent Literature 1: JP 2002-238887 A

SUMMARY OF INVENTION

Technical Problem

In an endoscopic examination, sizes and colors of lesions such as tumors are vital for diagnosis.

However, a site of interest examined by an endoscope may change in size and color according to distance from an imaging unit to an object. An endoscopic image obtained by an endoscope system in the related art does not reflect the absolute size and color of a tissue to be examined. For this reason, even when an operator examines an endoscopic image displayed on a monitor, the operator may misperceive the size and color of the site of interest.

An object of the present invention is to provide an endoscope system, a processor, a diagnostic support method, and a computer program capable of offering accurate diagnostic support information to an operator.

Solution to Problem

An endoscope system according to an aspect of the present invention includes: an endoscope; and a processor configured to process a captured image obtained from the endoscope, in which the endoscope includes: an imaging unit configured to capture an image of an object; and a focal length changing unit configured to change focal lengths of the imaging unit to change focal positions on the object along a direction of optical axis of the imaging unit, and the processor includes: an image obtaining unit configured to obtain a plurality of captured images captured at different focal positions on the object from the imaging unit; an evaluation value calculation unit configured to calculate an evaluation value indicating a degree of focus for each of corresponding sub-regions among the plurality of captured images; a determination unit configured to determine a captured image including a sub-region having the highest degree of focus among the plurality of captured images based on the calculated evaluation value of the sub-region; a distance calculation unit configured to calculate a distance to a region on the object corresponding to the sub-region based on an imaging condition when the captured image is captured; a distance information generation unit configured to generate distance information to the object by calculating a distance to a plurality of regions on the object corresponding to the sub-region; an extraction unit configured to extract a feature region from the captured image; a diagnostic support unit configured to generate diagnostic support information for the object based on the distance information generated by the distance information generation unit and a feature parameter associated with the feature region extracted by the extraction unit; and an output unit configured to output the diagnostic support information generated by the diagnostic support unit.

A processor according to an aspect of the present invention is connected to an endoscope and configured to process a plurality of captured image obtained from the endoscope, in which the endoscope includes: an imaging unit configured to capture an image of an object; and a focal length changing unit configured to change focal lengths of the imaging unit to change focal positions on the object along a direction of optical axis of the imaging unit, and the processor includes: an image obtaining unit configured to obtain a plurality of captured images captured at different focal positions on the object from the imaging unit; an evaluation value calculation unit configured to calculate an evaluation value indicating a degree of focus for each of corresponding sub-regions among the plurality of captured images; a determination unit configured to determine a captured image including a sub-region having the highest degree of focus among the plurality of captured images based on the calculated evaluation value of the sub-region; a distance calculation unit configured to calculate a distance to a region on the object corresponding to the sub-region based on an imaging condition when the captured image is captured; a distance information generation unit configured to generate distance information to the object by calculating a distance to a plurality of regions on the object corresponding to the sub-region; an extraction unit configured to extract a feature region from the captured image; a diagnostic support unit configured to generate diagnostic support information for the object based on the distance information generated by the distance information generation unit and a feature parameter associated with the feature region extracted by the extraction unit; and an output unit configured to output the diagnostic support information generated by the diagnostic support unit.

A diagnostic support method according to an aspect of the present invention involves: obtaining a plurality of captured images captured at different focal positions on an object from an imaging unit of an endoscope; calculating an evaluation value indicating a degree of focus for each of corresponding sub-regions among the plurality of captured images; determining a captured image including a sub-region having the highest degree of focus among the plurality of captured images based on the calculated evaluation value of the sub-region; calculating a distance to a region on the object corresponding to the sub-region based on an imaging condition when the captured image is captured; generating distance information to the object by calculating a distance to a plurality of regions on the object corresponding to the sub-region; extracting a feature region from the captured image; generating diagnostic support information for the object based on the distance information to the object and a feature parameter associated with the feature region; and outputting the generated diagnostic support information.

A computer program according to an aspect of the present invention causes a computer to execute processing involving: obtaining a plurality of captured images captured at different focal positions on an object from an imaging unit of an endoscope; calculating an evaluation value indicating a degree of focus for each of corresponding sub-regions among the plurality of captured images; determining a captured image including a sub-region having the highest degree of focus among the plurality of captured images based on the calculated evaluation value of the sub-region; calculating a distance to a region on the object corresponding to the sub-region based on an imaging condition when the captured image is captured; generating distance information to the object by calculating a distance to a plurality of regions on the object corresponding to the sub-region; extracting a feature region from the captured image; generating diagnostic support information for the object based on the distance information to the object and a feature parameter associated with the feature region; and outputting the generated diagnostic support information.

Advantageous Effects of Invention

According to the aspects of the present invention, it is possible to provide an operator with accurate diagnostic support information.

BRIEF DESCRIPTION OF DRAWINGS

FIG. 12 is a diagram for describing a display example according to a fifth embodiment.

DESCRIPTION OF EMBODIMENTS

Hereinafter, the present invention will be specifically described with reference to the drawings illustrating embodiments of the invention.

First Embodiment

Figure 1:
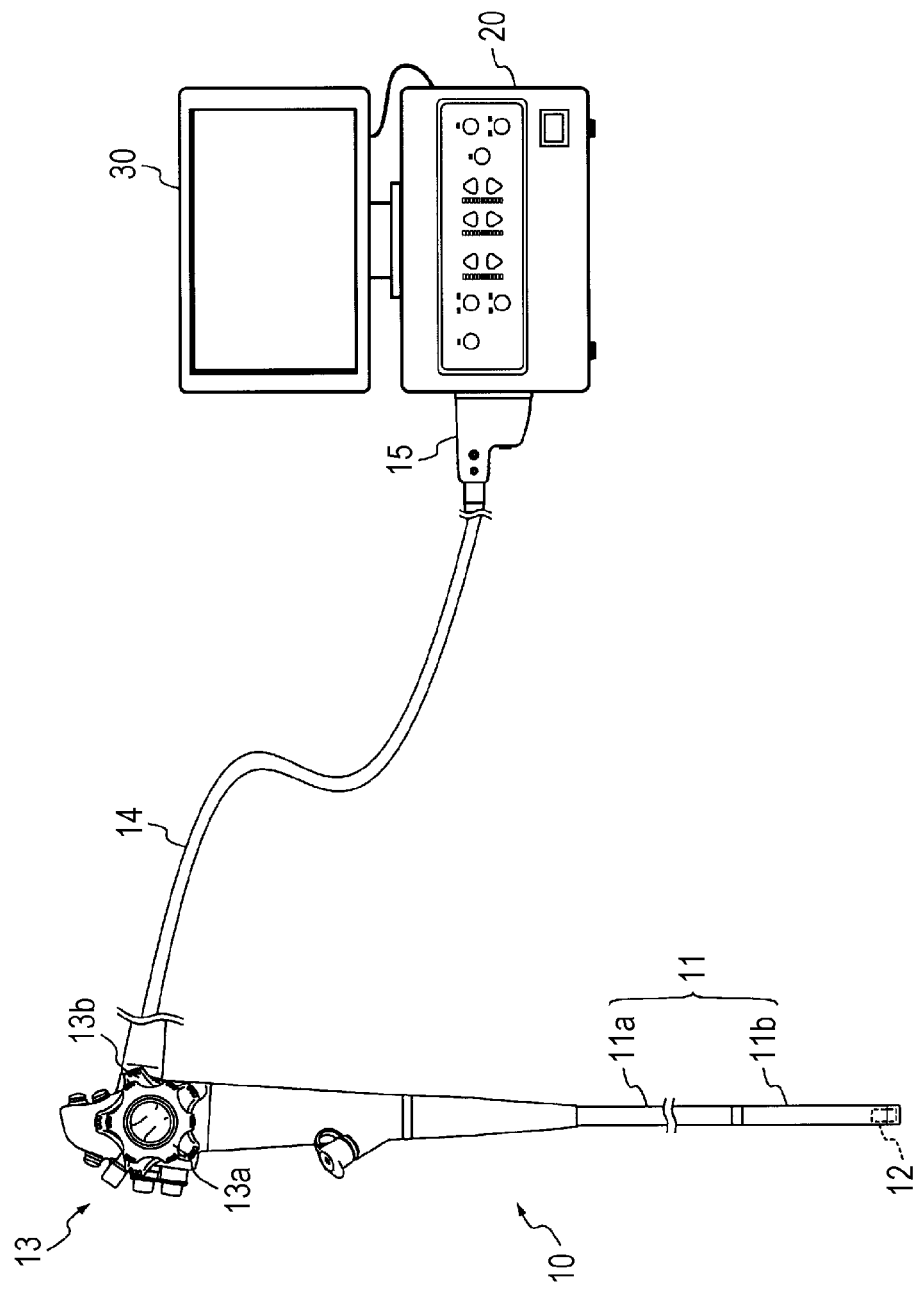
FIG. 1 is a schematic view for describing a configuration of an endoscope system.

FIG. 1 is a schematic view for describing a configuration of an endoscope system. The endoscope system according to a first embodiment includes an endoscope 10 for examining an object and a processor 20 for processing image data of an endoscopic image output from the endoscope 10. A monitor 30 is connected to the processor 20 and displays information to be given to an operator (such as a doctor) who operates the endoscope 10.

The endoscope 10 includes an endoscope insertion portion 11 which is inserted inside the object, an imaging unit 12 built into a distal tip of the endoscope insertion portion 11, an operation unit 13 disposed at a rear end part of the endoscope insertion portion 11 and operated by the operator, a universal cord 14 which transmits various kinds of information sent to and received from the processor 20, and a scope connector 15 which connects the endoscope 10 to the processor 20 electrically and optically. In this embodiment, the object captured by the endoscope 10 is, for example, a tissue inside a human body. The object is not limited to a tissue inside a human body and may be a tissue inside an organism or a structure other than the organism.

The endoscope insertion portion 11 includes a flexible tube 11a connected to the operation unit 13 and formed relatively long and a bending section 11b coaxially connected to the flexible tube 11a and formed relatively short and bendable. The flexible tube 11a is formed, for example, by covering a spiral tube with a reticular tube to form a flexible tube material and by covering an outer peripheral surface of the flexible tube material with a flexible resin casing. The bending section 11b is formed, for example, by covering a plurality of joint rings connected to each other in an inclinable manner with a reticular tube to form a bending pipe and by covering an outer peripheral surface of the bending pipe with a flexible and elastic rubber casing. A bending mechanism in the bending section 11b is a known mechanism incorporated in a typical endoscope and is configured to bend the bending section 11b when an operation wire is pulled in conjunction with an operation of the operation unit 13. The distal tip of the endoscope insertion portion 11 faces in different directions according to bending action caused by the operation, thereby moving an imaging region captured by the imaging unit 12.

The imaging unit 12 includes an image sensor 124 (see FIG. 2) such as complementary metal oxide semiconductor (CMOS) and outputs image data of a captured image of the object to the processor 20.

The operation unit 13 includes bending knobs 13a and 13b configured to receive an operation of bending the bending section 11b of the endoscope 10. The bending section 11b, for example, bends rightward and leftward according to rotation of the bending knob 13a and bends upward and downward according to rotation of the bending knob 13b. The rightward, leftward, upward, and downward directions in which the bending section 11b is bent are appropriately set relative to a direction in which the endoscope insertion portion 11 extends. In addition to the bending knobs 13a and 13b, the operation unit 13 may also include, for example, an air/water supply button for ejecting gas or liquid from the distal tip, a freeze button for switching between an examination image and a moving image or a still image, a zoom button for magnifying and minifying the examination image displayed on the monitor 30, and a button for switching between normal light and special light.

The processor 20 is a device including a light source unit 24 and an image processing unit 25 in an integrated manner. The light source unit 24 throws light into an inner portion of a subject which cannot catch natural light. The image processing unit 25 performs image processing on images captured by the endoscope 10 (see FIG. 2). Alternatively, the processor 20 may include a light source unit and an image processing unit separately.

The processor 20 extracts a feature region including a lesion such as a tumor from an image captured by the imaging unit 12 (also referred to as "endoscopic image") and generates diagnostic support information to be given to the operator of the endoscope 10. At this time, the processor 20 according to this embodiment generates distance information to the object based on images captured by the imaging unit 12. A method for generating distance information will be described in detail later. The processor 20 reflects the generated distance information in generation of diagnostic support information and corrects, for example, a small region of the lesion shown on a screen based on the distance information. Accordingly, it is possible to provide the operator with accurate diagnostic support information.

The monitor 30 is a device connected to the processor 20 and used for displaying images and various information output from the processor 20. The monitor 30 is a general-purpose display device such as a liquid crystal display device. Alternatively, the monitor 30 may be a device integrated with the processor 20.

Figure 2:
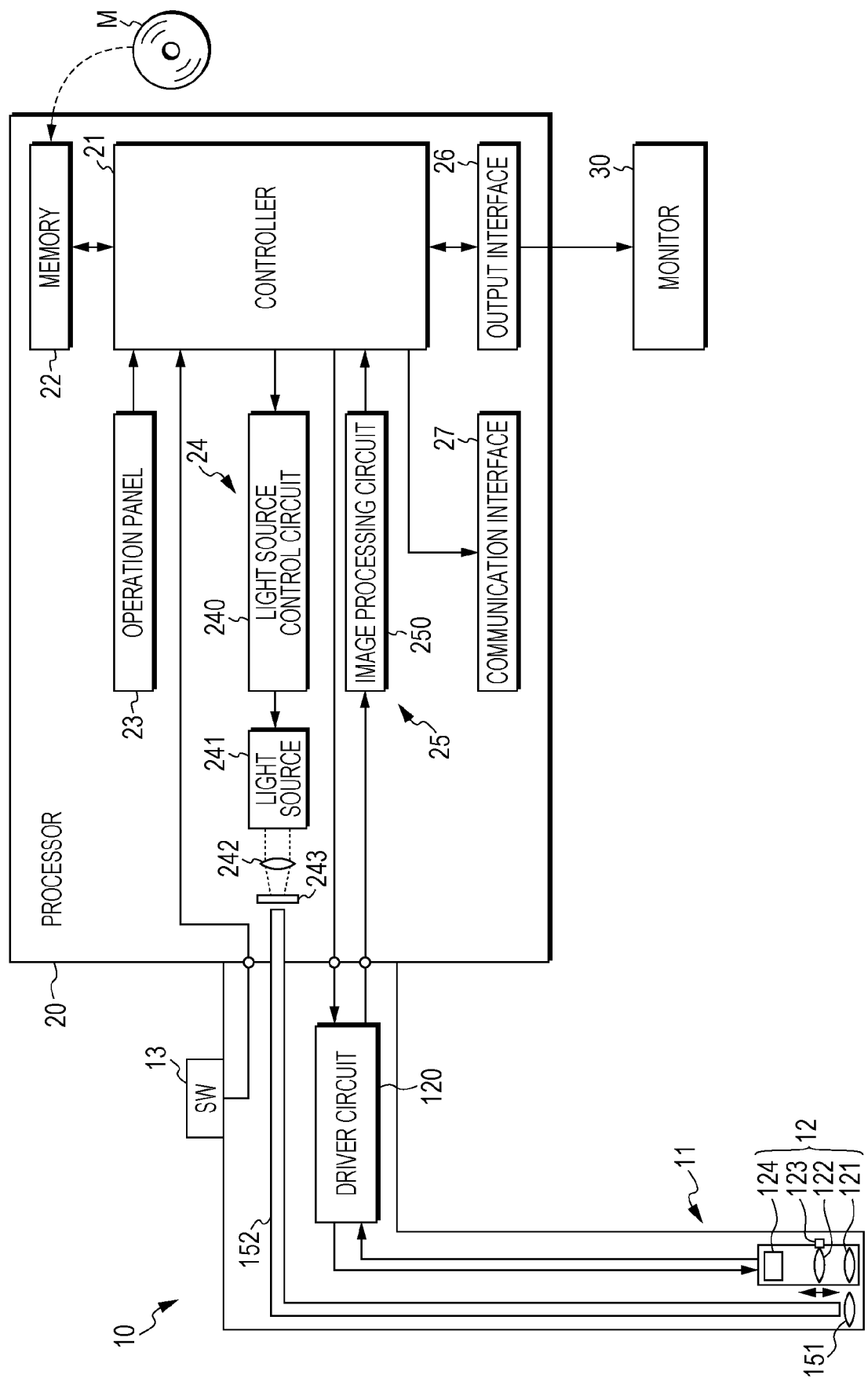
FIG. 2 is a block diagram illustrating internal configurations of an endoscope and a processor.

FIG. 2 is a block diagram illustrating internal configurations of the endoscope 10 and the processor 20. The imaging unit 12 of the endoscope 10 is disposed at the distal tip of the endoscope insertion portion 11. The imaging unit 12 is provided with, for example, a lens group including an objective lens 121 and a zoom lens 122, a lens drive mechanism 123 for moving the zoom lens 122 in a direction of optical axis, and the image sensor 124 such as CMOS. The objective lens 121 is disposed inside an examination window (not illustrated) disposed at the distal tip of the endoscope 10. The zoom lens 122 faces the objective lens 121. The zoom lens 122 is driven by the lens drive mechanism 123 to move freely between the telephoto end and the wide-angle end. The imaging unit 12 moves the zoom lens 122 to change focal lengths. While changing focal lengths, the imaging unit 12 captures images of the object to provide the processor 20 with a plurality of captured images of the object having different focal positions.

The imaging unit 12 is driven by a driver circuit 120. The driver circuit 120 is disposed in a connection part (inside the scope connector 15) with the processor 20 and includes, for example, a central processing unit (CPU), a timing generator (TG), and an analog signal processing circuit (AFE). The driver circuit 120 receives red, green, and blue (RGB) color signals output from the image sensor 124 according to clock signals output from the TG, performs necessary processing such as noise removal, amplification, and AD conversion to form digital format image data, and outputs the image data to the processor 20.

In addition, the endoscope 10 includes an illumination lens 151 and a light guide 152. The illumination lens 151 is disposed inside an illumination window disposed at the distal tip of the endoscope insertion portion 11. The light guide 152 includes, for example, a plurality of quartz optical fibers and is disposed inside the endoscope insertion portion 11, the operation unit 13, and the universal cord 14. Illumination light emitted from the light source unit 24 of the processor 20 is guided by the light guide 152 and diffused by the illumination lens 151, and then, the object is irradiated with the light through the illumination window.

The processor 20 includes, for example, a controller 21, a memory 22, an operation panel 23, the light source unit 24, the image processing unit 25, an output interface 26, and a communication interface 27.

The controller 21 includes, for example, a CPU, a read only memory (ROM), and a random access memory (RAM). A control program stored in the ROM in advance is developed into the RAM and executed by the CPU. Accordingly, the controller 21 controls operations of the aforementioned hardware.

The controller 21 is not limited to this configuration and may include at least one processing circuit including a graphics processing unit (GPU), a field programmable gate array (FPGA), a digital signal processor (DSP), a quantum processor, and a volatile or non-volatile memory. The controller 21 may also have functions of a clock that outputs information of the current time, a timer for measuring a time from the start of measurement to the end of measurement, and a counter for counting.

The memory 22 includes a non-volatile memory such as erasable programmable read only memory (EPROM). Instead of the non-volatile memory, the memory 22 may include, for example, a recording device equipped with a hard disk. The memory 22 stores, for example, data generated inside the processor 20 and data input from the outside. In another embodiment, the memory 22 may be a portable recording medium such as universal serial bus (USB) memory and secure digital (SD) card and may be removable from the processor 20.

The operation panel 23 includes, for example, various switches, buttons, and touch panel devices disposed in a housing of the processor 20. The operation panel 23 outputs to the controller 21 operation signals according to operations by the operator. The controller 21 controls operations of units in the endoscope 10 and the processor 20 according to operation signals output from the operation panel 23 and operation signals output from the operation unit 13 of the endoscope 10. In this embodiment, the operation panel 23 includes, for example, various switches, buttons, and touch panel devices disposed in the processor 20. However, alternatively, the operation panel 23 may include any input device such as mouse and keyboard connected to the processor 20.

The light source unit 24 includes, for example, a light source control circuit 240, a light source 241, a condenser lens 242, and a turret 243. The light source control circuit 240 is used for controlling operations of the light source 241 and the turret 243 by the control from the controller 21. The light source 241 is a high-luminance lamp such as xenon lamp, halogen lamp, and metal halide lamp, being configured to emit light having a spectrum ranging from the visible light region to the infrared light region. The light emitted from the light source 241 is collected by the condenser lens 242 and converted into light having appropriate properties through the rotary turret 243 equipped with filters. A motor is connected to the turret 243 through a transmission mechanism such as arm and gear. This motor is, for example, a DC motor and is configured to drive the turret 243 under control of the light source control circuit 240 to select a filter to be applied to emitted light.

The image processing unit 25 is provided with, for example, an image processing circuit 250 including a digital signal processor (DSP) and a digital image processor (DIP). The image processing unit 25 performs various kinds of processing on image data of images captured by the endoscope 10 such as color separation, color interpolation, gain correction, white balance adjustment, and gamma correction. The image processing unit 25 may also perform processing such as scaling, color enhancement, and edge enhancement. The image processing unit 25 outputs the processed image data to the controller 21.

The output interface 26 includes a processing circuit such as video processor. The output interface 26 converts image signals input from the controller 21 into video signals conforming to predetermined standards such as National Television System Committee (NTSC) and Phase Alternating Line (PAL). The output interface 26 sequentially outputs the converted video signals to the monitor 30, causing the monitor 30 to display an endoscopic image and diagnostic support information on the display screen.

The communication interface 27 includes a communication interface for transmitting and receiving various types of data to and from an external information processing device. Examples of the communication interface 27 include those conforming to LAN standards used in Wi-Fi (registered trademark) or Ethernet (registered trademark). Alternatively, communication interfaces conforming to other communication standards such as Bluetooth (registered trademark), ZigBee (registered trademark), 3G, 4G, 5G, and Long Term Evolution (LTE) may be employed as the communication interface 27.

The processor 20 in this embodiment (1) generates distance information to an object based on a plurality of images obtained by capturing images of the object at different focal positions, (2) extracts a feature region that may correspond to a lesion such as a tumor from each of the captured images, and (3) generates diagnostic support information based on the distance information to the object and a feature region parameter related to the feature region.

(1) Generation of Distance Information

Hereinafter, a method for generating distance information to an object will be described using an image captured by the endoscope 10.

Figure 3:
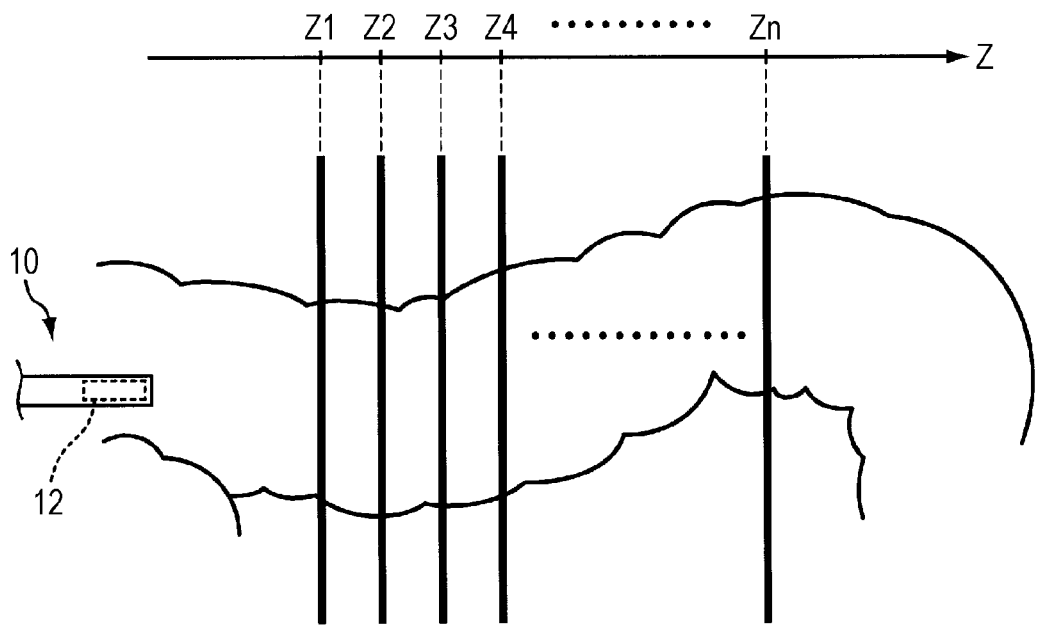
FIG. 3 is a diagram for describing procedures for capturing images of an object according to a first embodiment.

FIG. 3 is a diagram for describing procedures for capturing images of an object according to the first embodiment. The imaging unit 12 included in the endoscope 10 focuses on many focal planes opposing the image sensor 124 and captures images of an object under the control of the processor 20. For example, regarding the direction of optical axis of the imaging unit 12 as Z direction, the imaging unit 12 focuses on a focal plane at a position indicated by Z=Z1 and captures an image of the object, and then, output the captured image to the processor 20 through the driver circuit 120. The position indicated by Z=Z1 corresponds to, for example, a position where the imaging unit 12 has the shortest focal length.

Next, the imaging unit 12 changes positions of the focal plane from Z1 to Z2 (Z2>Z1). Focusing on a focal plane at a position indicated by Z=Z2, the imaging unit 12 captures an image of the object and outputs the captured image to the processor 20 through the driver circuit 120. While positions of the focal plane are changed from Z1 to Z2, the distal tip of the endoscope 10 is held not to move, and the position of the imaging unit 12 does not change.

After that, the imaging unit 12 captures images of the object in a similar manner to the above procedure while gradually shifting positions of the focal plane from Z=Z3, Z4, . . . , to Zn (n is, for example, 50), and then, outputs the captured images to the processor 20. The position indicated by Z=Zn corresponds to, for example, a position where the imaging unit 12 has the longest focal length.

In the above example, images of the object are captured while the focal length is gradually increased from the wide-angle end to the telephoto end, but images of the object may be captured while the focal length is gradually decreased from the telephoto end to the wide-angle end.

The number of images captured at different focal positions is, for example, 50 but is not limited to 50 and may be set optionally. Furthermore, the focal positions may be shifted at regular intervals (for example, a distance corresponding to 1 mm in the focal length) or may be changed according to focal length.

Figure 4:
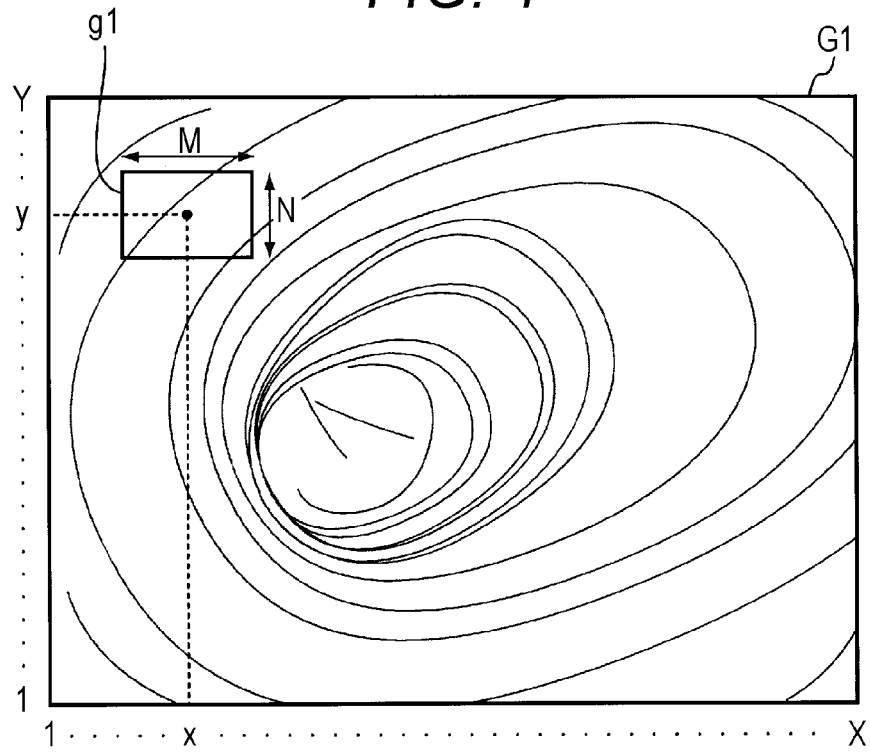
FIG. 4 is a schematic view illustrating an example of a captured image obtained by the processor.

From the imaging unit 12, the processor 20 obtains a plurality of images of the object captured at different focal positions. FIG. 4 is a schematic view illustrating an example of a captured image obtained by the processor 20. A captured image G1 illustrated in FIG. 4 is an image captured by focusing on, for example, the focal plane at the position indicated by Z=Z1. The captured image G1 is a digital format image including X pixels (for example, 1920 pixels) in a width direction and Y pixels (for example, 1080 pixels) in a height direction.

The processor 20 cuts out a sub-region g1 from the captured image G1 in order to evaluate a degree of focus. In FIG. 4, for example, a region having the center pixel at (x, y) coordinate, a width of M pixels (for example, 40 pixels), and a height of N pixels (for example, 20 pixels) is cut out as the sub-region g1.

FIG. 4 illustrates the image G1 captured by focusing on the focal plane indicated by Z=Z1. Note that images captured by focusing on the focal planes indicated by Z=Z2, Z3, . . . , and Zn are evaluated in a similar manner to the captured image G1.

The processor 20 evaluates a degree of focus of a sub-region cut out from each captured image and calculates a distance to the object based on the obtained evaluation value (hereinafter referred to as the focus evaluation value).

Figure 5:
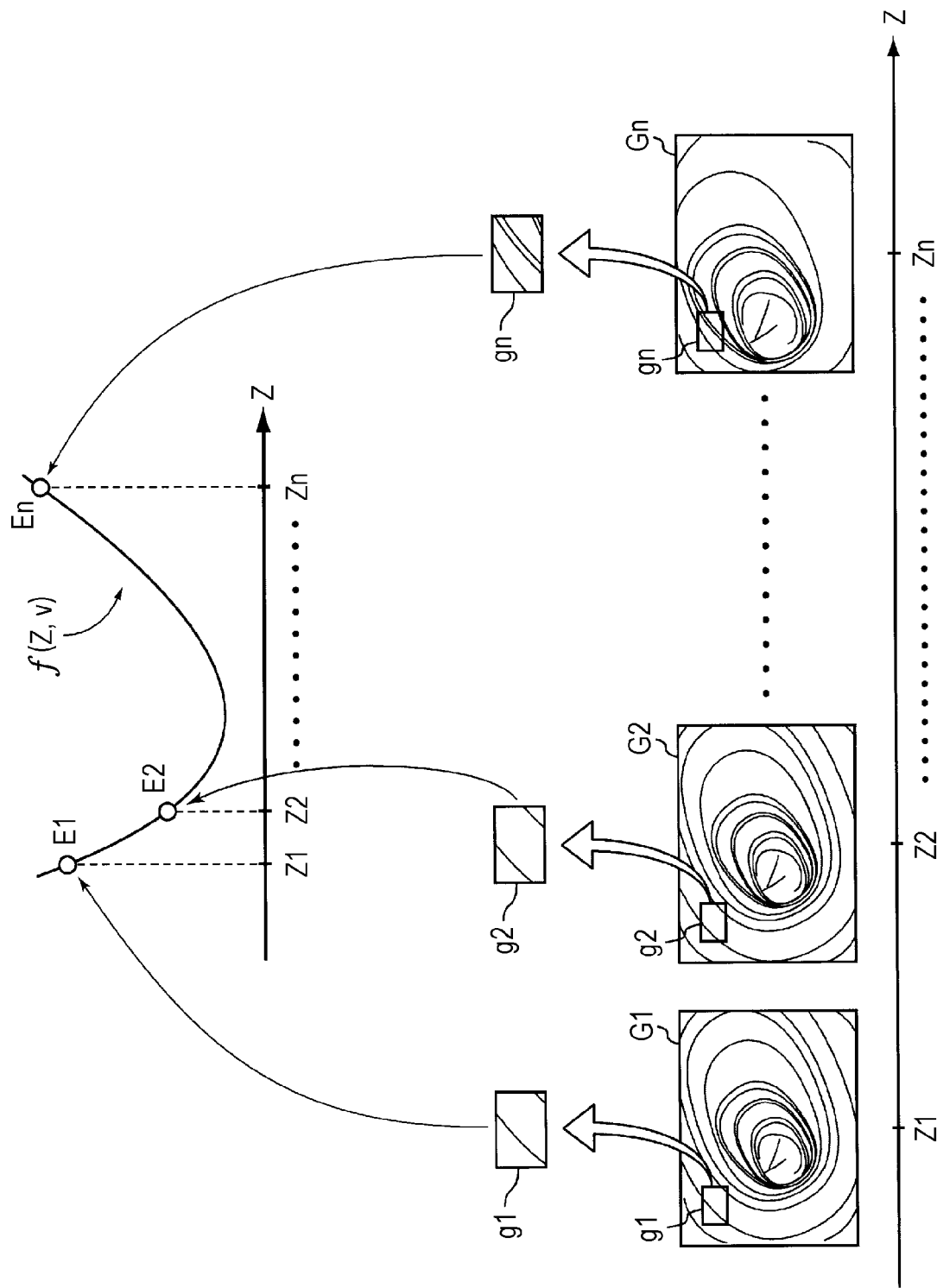
FIG. 5 is a diagram for describing a method for evaluating a degree of focus.

FIG. 5 is a diagram for describing a method for evaluating a degree of focus. The controller 21 of the processor 20 sequentially obtains the images captured as described above from the imaging unit 12. In other words, the controller 21 sequentially obtains the image G1 captured by focusing on the focal plane at the position indicated by Z=Z1, an image G2 captured by focusing on the focal plane at the position indicated by Z=Z2, . . . , and an image Gn captured by focusing on the focal plane at the position indicated by Z=Zn.

The controller 21 cuts out corresponding sub-regions g1, g2, . . . , and gn from the captured images G1, G2, . . . , and Gn, respectively. In other words, the controller 21 cuts out the sub-regions g1, g2, . . . , and gn from the captured images G1, G2, . . . , and Gn, respectively, in such a manner that the sub-regions g1, g2, . . . , and gn are all equal in coordinate (x, y) of the center pixel, in width M, and in height N.

The controller 21 calculates a focus evaluation value representing a degree of focus of each of the sub-regions g1, g2, . . . , and gn. As the focus evaluation value, an image entropy may be employed. The smaller the value of image entropy, the higher the degree of focus, and the larger the value of image entropy, the lower the degree of focus. An image entropy is represented by, for example, the following Formula 1.

$$E(v) = \sum_{j=1}^{M}\sum_{i=1}^{N}(-Gnor(i, j, v) \cdot \log_e Gnor(i, j, v)) \quad \text{[Formula 1]}$$

Here, E(v) is an image entropy of an image captured at a depth of field v. N and M are sizes of a sub-region. In the above example, N=40 and M=20. Furthermore, Gnor (i, j, v) is a pixel value of a normalized image and is represented by the following Formula 2.

$$Gnor(i, j, v) = \frac{G(i, j, v)}{\sum_{j=1}^{M} \sum_{i=1}^{N} G(i, j, v)} \quad \text{[Formula 2]}$$

Here, G (i, j, v) is a pixel value of a pixel specified by coordinate (i, j) in the sub-region.

According to Formulae 1 and 2, the controller 21 calculates image entropy values E1, E2, ..., and En from the sub-regions g1, g2, ..., and gn, respectively. The controller 21 compares the calculated image entropy values E1, E2, ..., and En and determines a captured image having the highest degree of focus from the sub-regions g1, g2, ..., and gn. At this time, the controller 21 plots the image entropy values E1, E2, ..., and En on a graph, having Z direction taken along the abscissa and the image entropy taken along the ordinate, and then, obtains an approximate curve f(Z, v) approximating each of the plotted values so as to obtain a focal position having the smallest image entropy. Among the captured images G1, G2, ..., and Gn, the controller 21 determines a captured image focusing on a focal plane closest to the obtained focal position as one including a sub-region having the highest degree of focus.

Instead of calculating image entropies represented by Formula 1, the controller 21 may calculate an image entropy for each color component of RGB and may synthesize the calculated image entropies of the color components. For example, when image entropies of RGB color components are E(R), E(G), and E(B), the controller 21 may calculate $E=[E(R)^2+E(R)^2+E(R)^2]^{1/2}$ where E represents an image entropy after the synthesis. The controller 21 determines a sub-region having the highest degree of focus by determining a sub-region having the smallest image entropy E after the synthesis.

Alternatively, the controller 21 may convert RGB components into YUV components and calculate an image entropy E(Y) of the Y component. The controller 21 determines a sub-region having the highest degree of focus by determining a sub-region having the smallest image entropy E(Y) after the calculation.

When the controller 21 determines a captured image including a sub-region having the highest degree of focus, the controller 21 uses an imaging condition (for example, focal length) at the time of capturing the image, thereby calculating a distance to a region on the object corresponding to the sub-region. For example, in a case where the optical system of the imaging unit 12 is a thin convex lens, the relation 1/D+1/c=1/f holds true between "D" a distance from the lens to the object, "f" a focal length, and "c" a screen distance (image distance). Using this relation, it is possible to calculate a distance to the object. The controller 21 causes the memory 22 to store the calculated distance as a distance in the sub-region.

Next, in predetermined units, the controller 21 gradually shifts center pixel positions of each of the sub-regions g1, g2, ..., and gn cut out from the captured images G1, G2, ..., and Gn and calculates a distance at each position, thereby obtaining distance information of the object. At this time, the controller 21 may shift center pixel positions of each of the sub-regions g1, g2, ..., and gn in units of, for example, M pixels in X direction and N pixels in Y direction and may calculate a distance for each region. Alternatively, the controller 21 may shift center pixel positions of each of the sub-regions g1, g2, ..., and gn per pixel in X direction and per pixel in Y direction and may calculate a distance for each pixel. The controller 21 may generate a distance image in which per-region or per-pixel distance information is stored.

(2) Extraction of Feature Region

From the captured images G1, G2, ..., and Gn, the controller 21 of the processor 20 extracts a feature region that may correspond to a lesion such as a tumor. For example, as disclosed in JP 6125740 B2, in a color plane defined by at least two color components among three of more color components, based on an angle formed by a line segment joining a reference point on the color plane and a corresponding point of each pixel and by a reference axis having a relation with a target disease, the controller 21 obtains an evaluation result of each pixel associated with the target disease, thereby extracting a feature region. The extraction by the controller 21 is not limited to the above method. The controller 21 may extract a feature region by a known method.

The controller 21 causes the memory 22 to store information of the feature region extracted from the captured images G1, G2, ..., and Gn (for example, pixel information corresponding to the feature region).

In this embodiment, the feature region is extracted from the captured images G1, G2, ..., and Gn, but a feature region may be extracted from an image captured at a specific focal length (for example, the captured image G1).

(3) Generation of Diagnostic Support Information

The controller 21 of the processor 20 generates diagnostic support information based on the distance information obtained from the captured images G1, G2, ..., and Gn and a feature parameter associated with the feature region extracted from the captured images G1, G2, ..., and Gn.

Endoscopic images (captured images) differ in apparent area according to distance to an object. In other words, the farther the distance to the object, the smaller the apparent area, and the shorter the distance to the object, the larger the apparent area. Therefore, the controller 21 may correct the apparent area (feature parameter) of a feature region in a captured image according to distance to the object.

For example, when a calculated distance to the object is r1 and a reference distance is r0, the controller 21 scales an area of a feature region at a ratio of $(r1/r0)^2$. As a method for scaling a feature region, nearest neighbor interpolation is employed. Nearest neighbor interpolation is a linear interpolation method in which enlarged or reduced pixels divided at a scaling ratio are rounded off and the obtained pixel coordinates are used. Alternatively, the scaling of a feature region may employ, for example, bilinear interpolation, bicubic interpolation, or Lanczos interpolation.

In the above example, a feature region is scaled, but the entire image including a feature region may be scaled.

Furthermore, endoscopic images (captured images) differ in chromaticity according to distance to an object. In other words, the farther the distance to the object, the lower the chromaticity of the corresponding image area, and the shorter the distance to the object, the higher the chromaticity of the corresponding image area. Therefore, the controller 21 may correct pixel values (feature parameter) in a feature region according to distance to the object.

Hereinafter described is, for example, correction processing when a reddened mucosal surface is extracted as a feature region. The controller 21 refers to the distance information corresponding to the extracted feature region and determines whether a distance to the reddened mucosal surface is equal to or more than a reference distance. Note that the reference distance is set in advance. In a case where a distance to the reddened mucosal surface is equal to or more than the reference distance, the mucosal surface may appear darker than its actual color. Accordingly, the controller 21 corrects each pixel within the feature region to increase a pixel value of R pixel. Contrary to this situation, in a case where a distance to the reddened mucosal surface is less than the reference distance, the mucosal surface may appear brighter than its actual color. Accordingly, the controller 21 corrects each pixel within the feature region to decrease a pixel value of R pixel.

When correcting a pixel value of R pixel, the controller 21 may change correction ratios according to distance. In other words, the controller 21 may increase the strength of the correction for a longer distance (or shorter distance).

When correcting a pixel value of R pixel, the controller 21 may change correction ratios according to ratio of R pixel. For example, when a distance to the mucosal surface is 1 time or more the reference distance and less than 2 times the reference distance, the controller 21 may obtain a ratio for correcting R by the expression R/(R+G+B). Furthermore, when a distance to the mucosal surface is 2 times or more the reference distance and less than 3 times the reference distance, the controller 21 may obtain a ratio for correcting R by the expression 2R/(R+G+B). Still further, when a distance to the mucosal surface is 3 times or more the reference distance and less than 4 times the reference distance, the controller 21 may obtain a ratio for correcting R by the expression 3R/(R+G+B).

The controller 21 generates diagnostic support information based on an endoscopic image (captured image) in which a feature parameter associated with a feature region is corrected. In generating diagnostic support information, the controller 21 uses a learning model 100 (see FIG. 6) configured to output information associated with a lesion in a body cavity in response to an input of an endoscopic image (captured image) to support diagnosis. The learning model 100 may be included in the processor 20 or in an external server accessible from the processor 20. In the former case, the learning model 100 is stored in the memory 22 of the processor 20 and used by access from the controller 21. In the latter case, the learning model 100 is stored in a storage device of the external server and used by access from the controller 21 through the communication interface 27.

Figure 6:
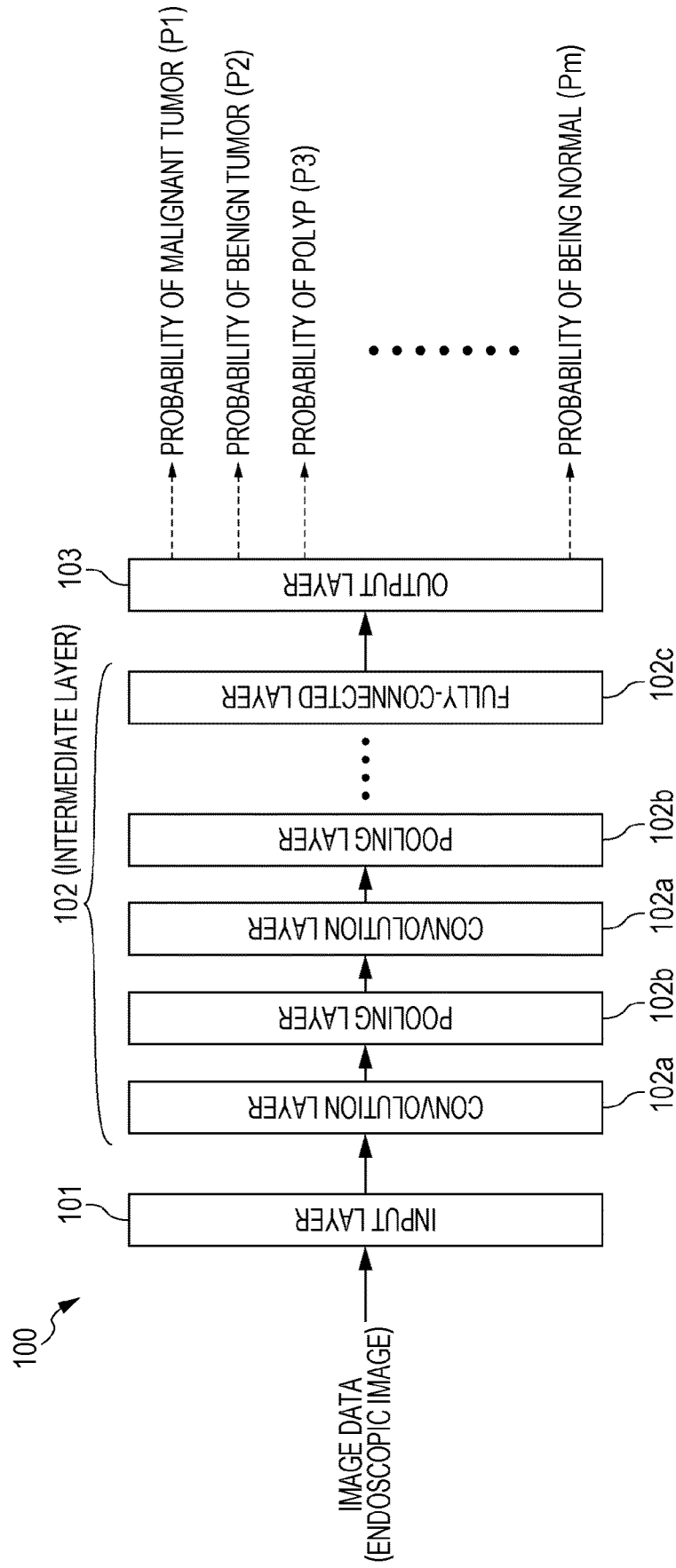
FIG. 6 is a configuration diagram illustrating an example of a learning model.

FIG. 6 is a configuration diagram showing an example of the learning model 100. Convolutional Neural Networks (CNN) or other neural networks are used to create the learning model 100. The learning model 100 includes an input layer 101, an intermediate layer 102, and an output layer 103. The learning model 100 is pre-trained to output information associated with a lesion in a body cavity in response to an input of an endoscopic image having a corrected feature parameter.

Image data of the endoscopic image with the corrected feature parameter is input to the input layer 101. The image data of the endoscopic image input to the input layer 101 is sent to the intermediate layer 102.

The intermediate layer 102 includes, for example, a convolution layer 102*a*, a pooling layer 102*b*, and a fully-connected layer 102*c*. A plurality of convolution layers 102*a* and pooling layers 102*b* may be disposed alternately. The convolution layer 102*a* and the pooling layer 102*b* extract a feature region of the endoscopic image input through the input layer 101 by calculation using a node of each layer. Data having the feature portion region extracted by the convolution layer 102*a* and the pooling layer 102*b* is combined into one node by the fully-connected layer 102*c*, and then, the fully-connected layer 102*c* outputs a feature variable converted by an activation function. The feature variable is output to the output layer 103 through the fully-connected layer 102*c*.

The output layer 103 includes one or more nodes. The output layer 103 uses a Softmax function to convert the feature variable input from the fully-connected layer 102*c* of the intermediate layer 102 into a probability. From each node, the output layer 103 outputs the probability for a category in which the endoscopic image belongs. Categories for classifying an endoscopic image may be set optionally. For example, categories may include malignant tumor, benign tumor, and polyp. In addition, categories of classification may include normal condition which is not belong in lesion categories.

FIG. 6 shows the learning model 100 in which the number of categories for classifying an endoscopic image is set to "m". This learning model 100 is configured to output a probability of malignant tumor P1, a probability of benign tumor P2, a probability of polyp P3, . . . , and a probability of being normal Pm from each node of the output layer 103. The number of categories (=m) to be set may be one or more.

Various parameters such as weight and bias that connect nodes are learned by a predetermined learning algorithm. In this embodiment, it is possible to collect a large amount of data including endoscopic images having a corrected feature parameter and doctor's diagnoses of the endoscopic images, and using these data as training data, it is possible to learn various parameters according to a predetermined learning algorithm.

The controller 21 of the processor 20 obtains the probability of each category from the output layer 103 of the learning model 100 and estimates the presence or absence of a lesion in a body cavity based on the obtained probability. For example, in a case where the probability of malignant tumor P1 exceeds a threshold (for example, 80%), the controller 21 infers that there is a malignant tumor in a body cavity of a subject. Any one of the probabilities P2, P3, . . . , and Pm−1 exceeding the threshold is inferred in a similar manner. On the other hand, in a case where none of the probabilities P1, P2, . . . , Pm−1 exceeds the threshold or where the probability Pm indicating normality exceeds the threshold, the controller 21 infers that there is no lesion within a range examined in an endoscopic image.

FIG. 6 illustrates the learning model 100 by CNN, but any machine learning model may be set for creating the learning model 100. For example, learning models based on Region-based CNN (R-CNN), You Only Look Once (YOLO), and Single Shot Detector (SSD) may be set as substitutes for CNN.

Furthermore, in this embodiment, the controller 21 is described as being configured to generate diagnostic information using the learning model 100. However, the controller 21 may be configured to determine the presence or absence of a lesion by comparing a preset reference value and information associated with a corrected feature region such as area and chromaticity, thereby outputting the determination result as diagnostic support information.

The controller 21 generates diagnostic support information based on information output from the learning model 100. The diagnostic support information is, for example, text data indicating an estimation result by the learning model 100. The diagnostic support information may be an image emphasizing a region inferred to be a lesion. The controller 21 outputs the generated diagnostic support information through the output interface 26, causing the monitor 30 to display the diagnostic support information.

Figure 7:
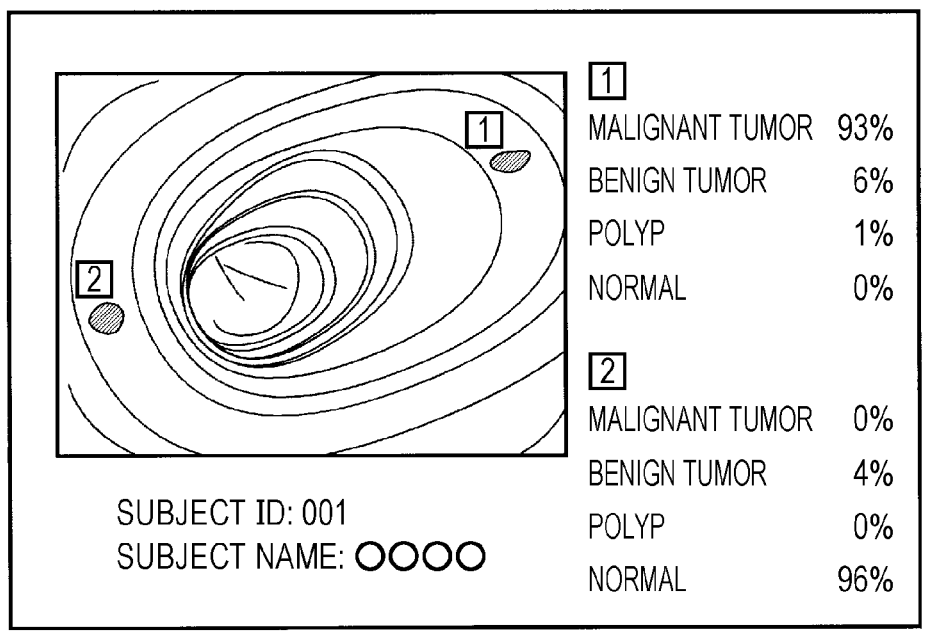
FIG. 7 is a schematic view illustrating a display example of diagnostic support information.

FIG. 7 is a schematic view illustrating a display example of diagnostic support information. FIG. 7 shows, for example, an endoscopic image having a feature parameter corrected and text data of estimation results by the learning model 100 with regard to each feature region indicated by indexes of "1" and "2".

Figure 8:
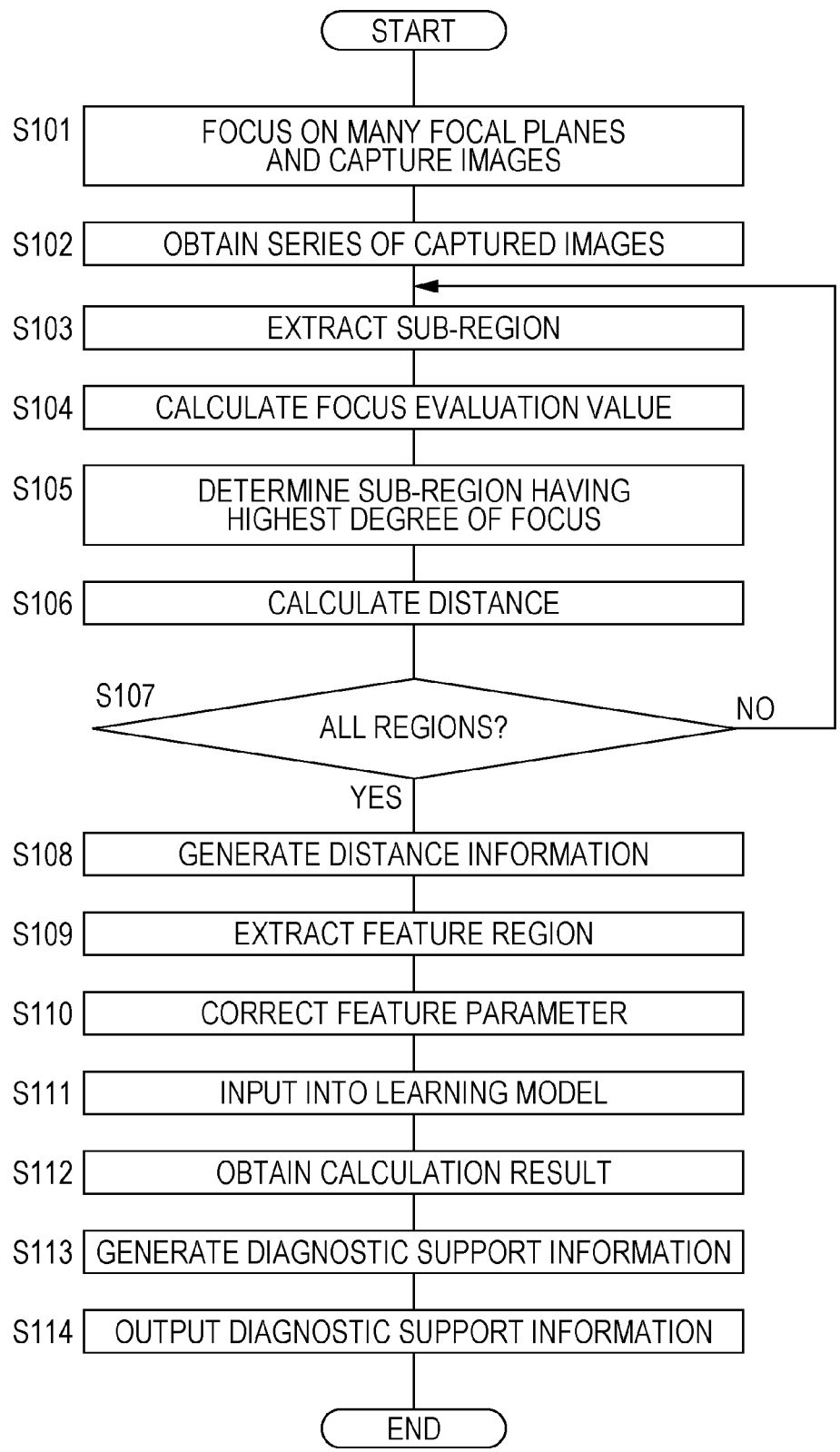
FIG. 8 is a flowchart for describing processing executed by the processor according to the first embodiment.

Procedures for processing executed by the processor 20 will now be described. FIG. 8 is a flowchart for describing the processing executed by the processor 20 according to the first embodiment. For example, with pressing operation of a release button of the endoscope 10, the controller 21 of the processor 20 focuses on many focal planes opposing the image sensor 124 and sequentially captures images of an object (step S101). At this time, to the driver circuit 120 of the endoscope 10, the controller 21 sends a control signal that gives an instruction to focus on many focal planes opposing the image sensor 124 and to capture images of the object sequentially. The driver circuit 120 drives the imaging unit 12 in response to the control signal from the controller 21, causing the imaging unit 12 to capture images.

Figure 9:
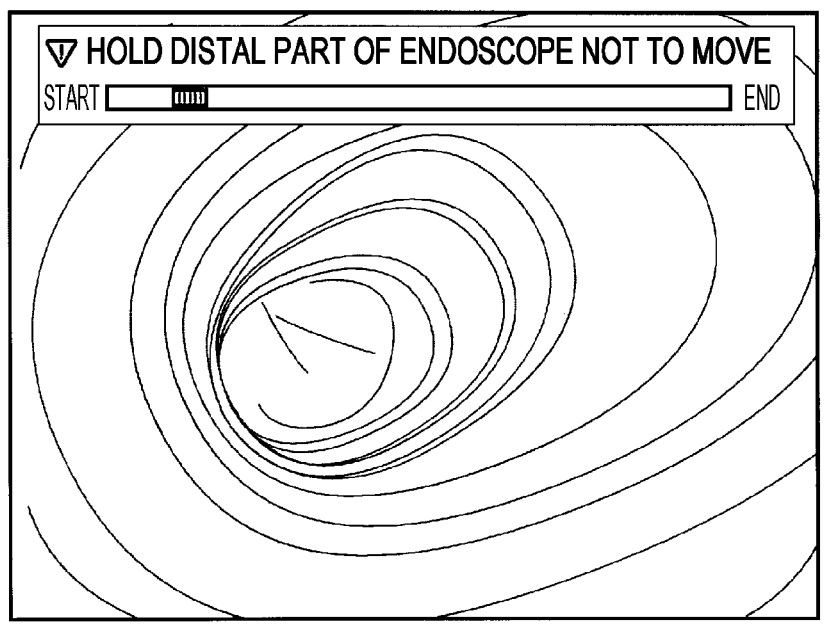
FIG. 9 is a schematic view illustrating a display example during image capturing.

The distal tip of the endoscope 10 is preferably held so as not to move while the imaging unit 12 is capturing images by focusing on many focal planes. Therefore, the controller 21 may give information that the distal tip of the endoscope 10 should be held not to move. FIG. 9 is a schematic view illustrating a display example during image capturing. The controller 21 creates a screen including text data indicating that the distal tip of the endoscope 10 should be held not to move and a slider visually indicating a period from the start of image capturing to the end of image capturing. The controller 21 outputs the created screen data from the output interface 26 to the monitor 30, thereby displaying an image as shown in FIG. 9.

The controller 21 obtains a series of images captured by the imaging unit 12 of the endoscope 10 (step S102). The series of captured images is stored in, for example, the memory 22.

The controller 21 cuts out corresponding sub-regions from the series of captured images (step S103) and calculates a focus evaluation value of each of the sub-regions (step S104). An example of the focus evaluation value includes an image entropy.

The controller 21 determines a sub-region having the highest degree of focus based on the calculated focus evaluation values (step S105). At this time, the controller 21 obtains a focal position having the smallest image entropy and determines an image captured on a focal plane closest to the obtained focal position as one including a sub-region having the highest degree of focus.

Next, the controller 21 uses an imaging condition (for example, focal length) at the time of capturing the image including the sub-region having the highest degree of focus, thereby calculating a distance to a region on the object corresponding to the sub-region (step S106). The controller 21 causes the memory 22 to store the calculated distance as a distance in the sub-region.

Next, the controller 21 determines whether distances are calculated for all regions in the captured images (step S107). In a case where there is an area with a distance yet to be calculated (S107: NO), the controller 21 resets a sub-region to be calculated and returns to step S103.

When distances of all regions in the captured images are calculated (S107: YES), distance information to the object is obtained. In other words, the controller 21 generates distance information to the object by storing a distance associated with each sub-region in a captured image (step S108).

Then, the controller 21 extracts from the captured image a feature region that may correspond to a lesion such as a tumor (step S109). The controller 21 extracts a feature region by a known method such as one disclosed in JP 6125740 B2.

Next, the controller 21 corrects a feature parameter associated with the feature region using the distance information generated in step S108 (step S110). At this time, the controller 21 may correct an area of the feature region or a pixel value as the parameter associated with the feature region. In a case where the controller 21 corrects an area of the feature region, an apparent area may be made larger when a distance to the object corresponding to the feature region is longer and an apparent area may be made smaller when a distance to the object corresponding to the feature region is shorter. In a case where the controller 21 corrects a pixel value of the feature region, an image of the feature region may be made brighter when a distance to the object corresponding to the feature region is longer and an image of the feature region may be made darker when a distance to the object corresponding to the feature region is shorter.

Next, the controller 21 inputs into the learning model 100 an endoscopic image obtained by correcting the feature parameter (step S111) and obtains a calculation result by the learning model 100 (step S112). In a case where the learning model 100 is stored in the memory 22 of the processor 20, the controller 21 inputs image data of the endoscopic image to the input layer 101 of the learning model 100 and executes calculations using the intermediate layer 102, thereby obtaining the calculation result from the output layer 103. In a case where the learning model 100 is stored in an external server, image data of the endoscopic image obtained by correcting the feature parameter is transmitted from the communication interface 27 to the external server, and the controller obtains the result calculated by the learning model 100 of the external server by communication.

The controller 21 generates diagnostic support information based on the calculation result of the learning model 100 (step S113) and outputs the generated diagnostic support information from the output interface 26 (step S114) to provide the operator with diagnostic support.

As described above, in this embodiment, it is possible to correct a feature parameter associated with a feature region based on distance information to an object. Furthermore, since calculation by the learning model 100 is executed using an endoscopic image having a corrected feature parameter, it is possible to enhance estimation accuracy by the learning model 100.

In this embodiment, an image entropy is used as an evaluation value for evaluating a degree of focus, but other evaluation values may be used. For example, image sharpness and an amount of contrast C(v) represented by the following Formula 3 may also be used as substitutes for an image entropy.

$$C(v) = \sum_{j=1}^{M}\sum_{i=1}^{N}(|Gnor(i, j, v) - Gnor(i-1, j, v)|^n$$
$$+ |Gnot(i, j, v) - Gnor(i, j-1, v)|^2 +$$
$$|Gnor(i, j, v) - Gnor(i+1, j, v)|^n +$$
$$|Gnor(i, j, v) - Gnor(i, j+1, v)|^n)$$

[Formula 3]

n is a natural number.

The lower the image sharpness or the smaller the amount of contrast, the lower the degree of focus, and the higher the image sharpness or the larger the amount of contrast, the higher the degree of focus. Therefore, when using these evaluation values, the controller 21 determines a sub-region having the highest image sharpness or the largest amount of contrast.

Second Embodiment

A second embodiment will illustrate a configuration for changing brightness levels during image capturing.

Figure 10:
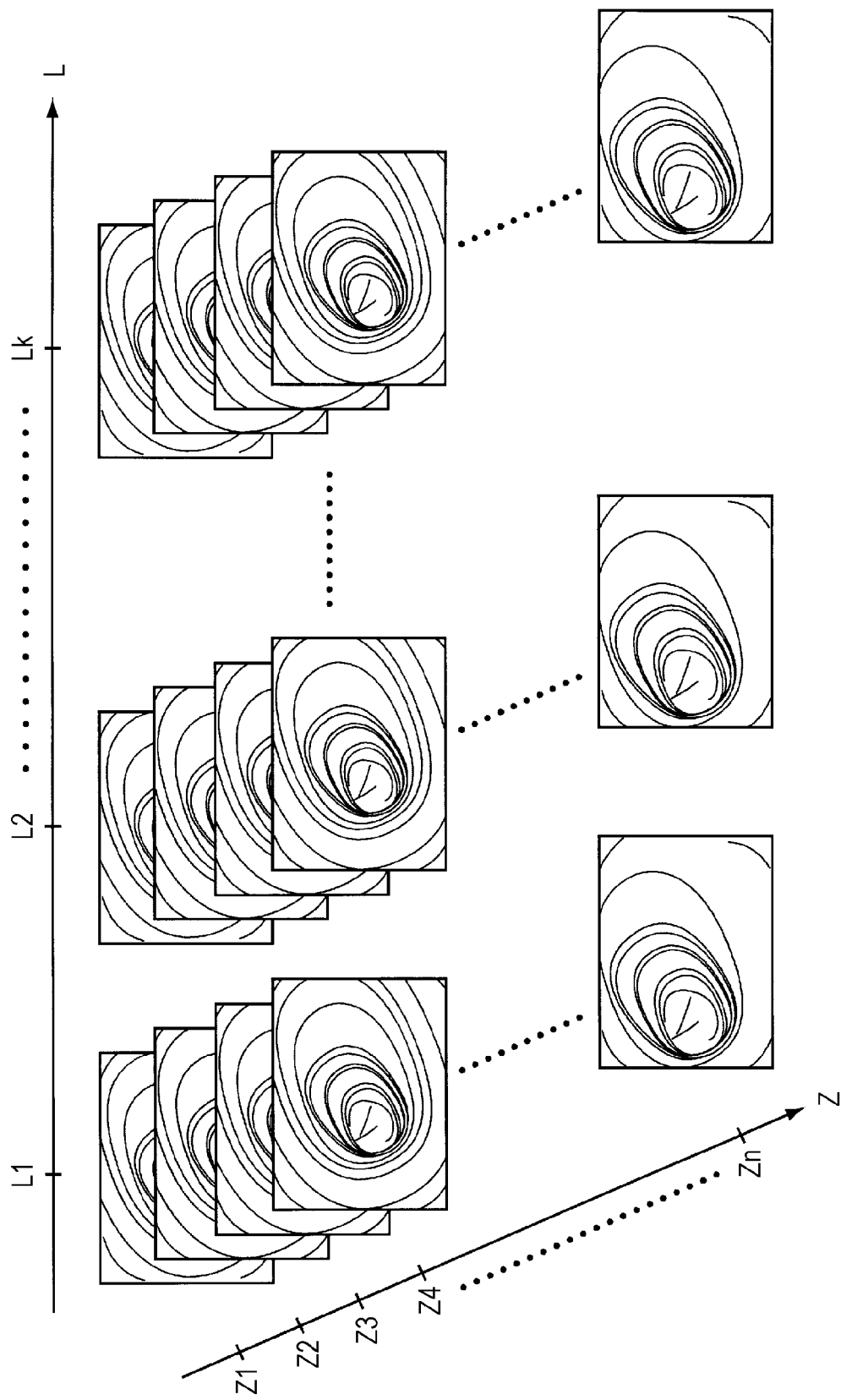
FIG. 10 is a diagram for describing procedures for capturing images of an object according to a second embodiment.

FIG. 10 is a diagram for describing procedures for capturing images of an object according to the second embodiment. The controller 21 of the processor 20 controls the driver circuit 120 of the endoscope 10 to capture an image of an object, focusing on many focal planes opposing the image sensor 124 and also controls the light source unit 24 to change brightness levels (quantities of light) during image capturing in a phased manner. The number of images captured at different focal positions is, for example, about 50, similarly to the first embodiment. The brightness levels may be changed in 2 to 5 phases.

For example, the imaging unit 12 focuses on the focal plane at the position indicated by Z=Z1, and the light source unit 24 gradually changes the brightness levels, for example, from L1, L2, . . . , to Lk to capture images of the object. Herein, L1, L2, . . . , and Lk are index values (for example, intensity of illumination) representing the brightness levels. The symbol k is, for example, an integer from 2 to 5. The brightness levels may be changed in the order of L1, L2, . . . , and Lk to show an image brighter or to show an image darker. The obtained captured images are output to the processor 20 through the driver circuit 120. The position indicated by Z=Z1 corresponds to, for example, a position where the imaging unit 12 has the shortest focal length. Note that the distal tip of the endoscope 10 is held not to move when the brightness levels are changed and that the imaging unit 12 does not change in position.

Next, the imaging unit 12 changes positions of the focal plane from Z1 to Z2 (Z2>Z1). Focusing on the focal plane at the position indicated by Z=Z2, the imaging unit 12 captures images of the object by gradually changing the brightness levels from L1, L2, . . . , to Lk. The obtained captured images are output to the processor 20 through the driver circuit 120. While changing positions of the focal plane from Z1 to Z2 and changing the brightness levels, the distal tip of the endoscope 10 is held not to move, and the position of the imaging unit 12 does not change.

After that, while gradually shifting the focal plane from positions indicated by Z=Z3, Z4, . . . , to Zn (n is, for example, 50) in a similar manner to the above procedures, the imaging unit 12 captures images of the object at each focal position by changing the brightness levels in a phased manner. The obtained captured images are output to the processor 20. The position indicated by Z=Zn corresponds to, for example, a position where the imaging unit 12 has the longest focal length.

The processor 20 obtains from the imaging unit 12 a plurality of images of the object captured at different focal positions and different brightness levels and generates distance information to the object from the captured images. A method for generating distance information is similar to the method in the first embodiment. In other words, corresponding sub-regions in the plurality of captured images having different focal positions and different brightness levels are cut out, and a degree of focus is evaluated for each of the sub-regions cut out, thereby generating distance information to the object.

Furthermore, in a similar manner to the first embodiment, the processor 20 corrects a feature parameter of a feature region in the captured images using the generated distance information, thereby generating diagnostic support information based on an endoscopic image having a corrected feature parameter.

As described above, the second embodiment enables brightness levels to be changed in a phased manner during image capturing. Accordingly, it is possible to avoid a situation that a degree of focus is not properly evaluated due to too bright an image (or too dark an image).

In this embodiment, an image of an object is captured by changing brightness levels at a fixed focal position. However, an image of an object may be captured by changing focal positions at a fixed brightness level.

Third Embodiment

A third embodiment will illustrate a configuration for removing or correcting a singular value included in a calculated distance.

Figure 11:
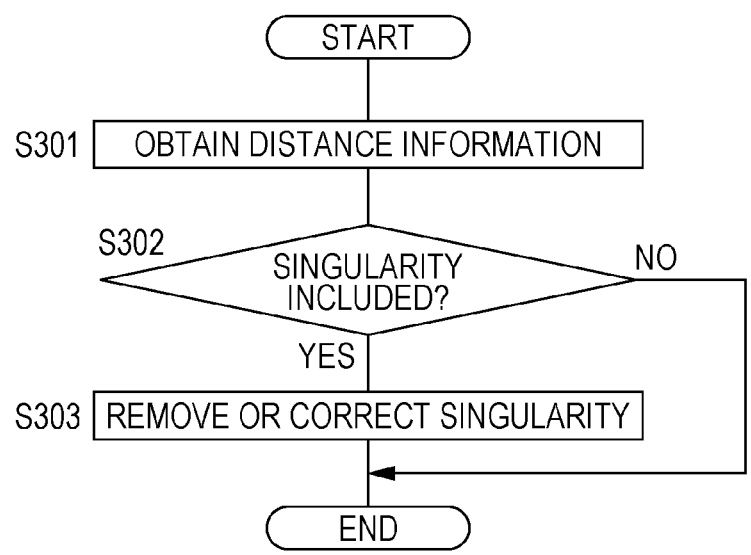
FIG. 11 is a flowchart for describing processing executed by a processor according to a third embodiment.

FIG. 11 is a flowchart for describing processing executed by the processor 20 according to the third embodiment. The controller 21 of the processor 20 obtains distance information to an object in a similar manner to the first embodiment (step S301). In other words, the controller 21 cuts out sub-regions from a series of images captured at different focal positions and evaluates a degree of focus for each of the sub-regions, thereby calculating a distance to a region on the object corresponding to each sub-region. The controller 21 generates distance information to the object by calculating distances of all regions in the captured images.

Next, the controller 21 determines whether the distance information includes a singularity (step S302). For example, the controller 21 calculates an average of the calculated distances. In a case where there is a point that deviates from the average by a predetermined value (for example, three times the standard deviation) or more, the controller 21 determines that the distance information includes a singularity.

Determining that the singularity is included (S302: YES), the controller 21 removes or corrects the singularity (step S303). At this time, the controller 21 may remove the singularity by deleting a value of a distance corresponding to the singularity. Alternatively, the controller 21 may correct a singular value by estimating a distance at the singularity using a distance calculated in the vicinity of the singularity and by rewriting the estimated distance as the distance at the singularity. Furthermore, the controller 21 may change brightness levels and capture images again to recalculate a distance at the singularity.

Determining in step S302 that the singularity is not included (S302: NO), or removing or correcting the singularity in step S303, the controller 21 ends the processing of this flowchart.

As described above, this embodiment enables removal or correction of a singularity based on distance information. Accordingly, it is possible to appropriately correct a feature parameter associated with a feature region.

Fourth Embodiment

A fourth embodiment will illustrate a method for changing brightness levels of an endoscopic image according to distance to the object.

In the endoscope 10, light emitted from the light source unit 24 may not reach a deep place sufficiently. For this reason, in an image captured by the endoscope 10, an image area in which a distance to the object is short tends to appear with a relatively high luminosity, and an image area in which a distance to the object is long tends to appear with a relatively low luminosity. Therefore, the controller 21 changes luminosities according to distance to the object. A distance to the object may be calculated in a manner similar to the first embodiment.

When a pixel in which a distance to the object is "r" has a pixel value of (R, G, B), the controller 21 corrects the pixel value by equations, for example, R'=R+n(r), G'=G+n(r), and B'=B+n(r). Herein, n(r) is a positive integer and is increased in a phased manner according to distance "r". For example, when 0≤r<r1, n(r) is 0, when r1≤r<r2, n(r) is 1, and when r2≤r<r3, n(r) is 2. The controller 21 may use a function to correct the pixel value or may use a table to correct the pixel value. The controller 21 corrects all pixels included in the image captured by the endoscope 10 or pixels included in a specific region.

With this correction, it is possible to correct the endoscopic image in such a manner that a larger "r" (that is, a longer distance to the object) enables a higher luminosity.

The controller 21 may set a threshold for the luminosity and perform correction processing for a pixel lower than the threshold. Furthermore, luminance may be corrected instead of the luminosity. For example, the controller 21 may convert RGB components into YUV components and correct a value of the Y component according to the distance r.

As described above, the fourth embodiment enables a deep examination area to be displayed brightly without producing a sense of incompatibility, which reduces the danger of overlooking of a lesion.

Fifth Embodiment

A fifth embodiment will illustrate a configuration for displaying an endoscopic image in three dimensions.

FIG. 12 is a diagram for describing a display example according to the fifth embodiment. As described in the first embodiment, the controller 21 calculates a distance to an object. FIG. 12 shows an example of an endoscopic image including two regions, that is, a region R1 in which a distance to an object is relatively short and a region R2 in which a distance to the object is relatively long. When an endoscopic image including the regions R1 and R2 is captured from the front as shown in the upper part of FIG. 12, it is difficult for an operator to distinguish between the region R1 and the region R2.

For this reason, the controller 21 uses distance information to the object and displays the endoscopic image in three dimensions. Specifically, based on the distance information, the controller 21 displays the endoscopic image in three dimensions by, for example, isometric drawing, dimetric drawing, or trimetric drawing.

The lower part of FIG. 12 shows an image drawn three-dimensionally by isometric drawing. Since the region R1 represents a relatively short distance to the object and the region R2 represents a relatively long distance to the object, when the regions R1 and R2 are drawn three-dimensionally, the region R1 is drawn as a region raised from the region R2. A height of the raised portion corresponds to a difference between a distance to the region R2 and a distance to the region R1. With the display of such a three-dimensional image, the operator can clearly recognize the existence of the region R1.

As described above, in the fifth embodiment, an endoscopic image is displayed in three dimensions based on distance information. Accordingly, it is possible to show the existence and height of a raised portion, which reduces the danger of overlooking a lesion.

The embodiments disclosed herein are considered to be in all respects as illustrative and not restrictive. The scope of the present invention is indicated by the scope of claims, not the aforementioned significance, and is intended to include all modifications within the significance and scope equivalent to the claims.

REFERENCE SIGNS LIST

10 Endoscope
11 Endoscope insertion portion
11a Flexible tube
11b Bending section
12 Imaging unit
13 Operation unit
14 Universal cord
15 Scope connector
20 Processor
21 Controller
22 Memory
23 Operation panel
24 Light source unit
25 Image processing unit
26 Output interface
27 Communication interface
30 Monitor
100 Learning model
M Recording medium

The invention claimed is:

1. An endoscope system comprising:
an endoscope; and
a processor configured to process a captured image obtained from the endoscope,
wherein the endoscope comprises:
an imaging unit configured to capture an image of an object; and
a focal length changing unit configured to change focal lengths of the imaging unit to change focal positions on the object along a direction of optical axis of the imaging unit, and
the processor comprises:
an image obtaining unit configured to obtain a plurality of captured images captured at different focal positions on the object from the imaging unit;
an evaluation value calculation unit configured to calculate an evaluation value indicating a degree of focus for each of corresponding sub-regions among the plurality of captured images;
a determination unit configured to determine a captured image including a sub-region having the highest degree of focus among the plurality of captured images based on the calculated evaluation value of the sub-region;
a distance calculation unit configured to calculate a distance to a region on the object corresponding to the sub-region based on an imaging condition when the captured image is captured;
a distance information generation unit configured to generate distance information to the object by calculating a distance to a plurality of regions on the object corresponding to the sub-region;
an extraction unit configured to extract a feature region from the captured image;

a diagnostic support unit configured to generate diagnostic support information for the object based on the distance information generated by the distance information generation unit and a feature parameter associated with the feature region extracted by the extraction unit; and an output unit configured to output the diagnostic support information generated by the diagnostic support unit.

2. The endoscope system according to claim 1, further comprising:

a light source configured to emit light with which the object is irradiated; and a light source control circuit configured to control a quantity of light emitted by the light source, wherein the image obtaining unit obtains a plurality of captured images of the object captured at different focal positions and with different quantities of light, and the evaluation value calculation unit calculates an evaluation value indicating a degree of focus for each of the corresponding sub-regions among the plurality of captured images having different focal positions and different quantities of light.

3. The endoscope system according to claim 1, wherein the processor comprises a detection unit configured to detect a singular value from the distance calculated by the distance calculation unit, and the distance information generation unit generates distance information obtained by removing or correcting the singular value detected by the detection unit.

4. The endoscope system according to claim 1, wherein the diagnostic support unit generates diagnostic support information for the object using a learning model configured to output an estimation result indicating presence or absence of a lesion in response to an input of the captured image.

5. The endoscope system according to claim 4, wherein the diagnostic support unit inputs into the learning model the captured image obtained by correcting the feature parameter based on the distance information.

6. The endoscope system according to claim 1, wherein the evaluation value includes any one of image entropy, image sharpness, and amount of contrast in the sub-region.

7. The endoscope system according to claim 1, wherein the processor comprises an information unit configured to give information indicating that image capturing is in progress while the imaging unit is capturing a plurality of captured images to be obtained by the image obtaining unit.

8. The endoscope system according to claim 1, wherein the processor comprises a correction unit configured to correct a pixel value of a pixel included in the captured image based on the distance information.

9. The endoscope system according to claim 1, wherein the processor comprises an image conversion unit configured to convert the captured image based on the distance information to display the captured image in three dimensions.

10. A processor connected to an endoscope and configured to process a plurality of captured image obtained from the endoscope, wherein the endoscope comprises:

an imaging unit configured to capture an image of an object; and a focal length changing unit configured to change focal lengths of the imaging unit to change focal positions on the object along a direction of optical axis of the imaging unit, and the processor comprises:

an image obtaining unit configured to obtain a plurality of captured images captured at different focal positions on the object from the imaging unit;

an evaluation value calculation unit configured to calculate an evaluation value indicating a degree of focus for each of corresponding sub-regions among the plurality of captured images;

a determination unit configured to determine a captured image including a sub-region having the highest degree of focus among the plurality of captured images based on the calculated evaluation value of the sub-region;

a distance calculation unit configured to calculate a distance to a region on the object corresponding to the sub-region based on an imaging condition when the captured image is captured;

a distance information generation unit configured to generate distance information to the object by calculating a distance to a plurality of regions on the object corresponding to the sub-region;

an extraction unit configured to extract a feature region from the captured image;

a diagnostic support unit configured to generate diagnostic support information for the object based on the distance information generated by the distance information generation unit and a feature parameter associated with the feature region extracted by the extraction unit; and an output unit configured to output the diagnostic support information generated by the diagnostic support unit.

11. A diagnostic support method comprising:

obtaining a plurality of captured images captured at different focal positions on an object from an imaging unit of an endoscope;

calculating an evaluation value indicating a degree of focus for each of corresponding sub-regions among the plurality of captured images;

determining a captured image including a sub-region having the highest degree of focus among the plurality of captured images based on the calculated evaluation value of the sub-region; calculating a distance to a region on the object corresponding to the sub-region based on an imaging condition when the captured image is captured;

generating distance information to the object by calculating a distance to a plurality of regions on the object corresponding to the sub-region;

extracting a feature region from the captured image;

generating diagnostic support information for the object based on the distance information to the object and a feature parameter associated with the feature region; and outputting the generated diagnostic support information.

* * * * *